(12) United States Patent
Anderson et al.

(10) Patent No.: US 8,663,222 B2
(45) Date of Patent: Mar. 4, 2014

(54) DYNAMIC AND STATIC BIPOLAR ELECTRICAL SEALING AND CUTTING DEVICE

(75) Inventors: Sara E. Anderson, Erie, CO (US); William H. Nau, Jr., Longmont, CO (US); Gary M. Couture, Longmont, CO (US); Rebecca Coulson, Lyons, CO (US)

(73) Assignee: Covidien LP, Mansfield, MA (US)

( * ) Notice: Subject to any disclaimer, the term of this patent is extended or adjusted under 35 U.S.C. 154(b) by 762 days.

(21) Appl. No.: 12/876,668

(22) Filed: Sep. 7, 2010

(65) Prior Publication Data
US 2012/0059371 A1    Mar. 8, 2012

(51) Int. Cl.
*A61B 18/14* (2006.01)
(52) U.S. Cl.
USPC .......................................................... 606/52
(58) Field of Classification Search
USPC .................................... 606/27, 34, 41, 51, 52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,151,102 A * | 9/1992 | Kamiyama et al. ............. 606/51 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,658,281 A * | 8/1997 | Heard .............................. 606/48 |
| D384,413 S | 9/1997 | Zlock et al. |
| 5,810,805 A | 9/1998 | Sutcu et al. |
| 5,810,811 A | 9/1998 | Yates et al. |
| D402,028 S | 12/1998 | Grimm et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Michael Peffley
*Assistant Examiner* — Daniel Fowler

(57) ABSTRACT

An end effector assembly includes opposed jaws moveable from an open to a closed position for grasping tissue therebetween. Each jaw includes an electrically conductive surface adapted to conduct electrosurgical energy through tissue disposed between the jaws. A static bipolar cutting portion including at least one electrically conductive cutting element and at least one insulating element having a first configuration is disposed on at least one of the jaws. The static cutting portion is configured to electrically cut tissue disposed between the jaws upon activation of the cutting element and at least one of an opposing sealing surface and an opposing cutting element. A dynamic cutting portion including at least one electrically conductive cutting element and at least one insulating element having a second configuration is disposed on at least one of the jaws. The dynamic cutting portion electrically transects tissue during movement relative to tissue.

10 Claims, 6 Drawing Sheets

(56) References Cited

U.S. PATENT DOCUMENTS

| | | | |
|---|---|---|---|
| D416,089 S | 11/1999 | Barton et al. | |
| D424,694 S | 5/2000 | Tetzlaff et al. | |
| D425,201 S | 5/2000 | Tetzlaff et al. | |
| 6,152,923 A * | 11/2000 | Ryan | 606/51 |
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| 6,736,813 B2 | 5/2004 | Yamauchi et al. | |
| D493,888 S | 8/2004 | Reschke | |
| D496,997 S | 10/2004 | Dycus et al. | |
| D499,181 S | 11/2004 | Dycus et al. | |
| 6,821,273 B2 | 11/2004 | Mollenauer | |
| D502,994 S | 3/2005 | Blake, III | |
| D509,297 S | 9/2005 | Wells | |
| 7,052,496 B2 * | 5/2006 | Yamauchi | 606/51 |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| 7,147,637 B2 * | 12/2006 | Goble | 606/50 |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| 7,232,440 B2 | 6/2007 | Dumbauld et al. | |
| D547,154 S | 7/2007 | Lee | |
| 7,270,664 B2 | 9/2007 | Johnson et al. | |
| D564,662 S | 3/2008 | Moses et al. | |
| D567,943 S | 4/2008 | Moses et al. | |
| 7,367,976 B2 | 5/2008 | Lawes et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 2002/0188294 A1 | 12/2002 | Couture et al. | |
| 2003/0018331 A1 | 1/2003 | Dycus | |
| 2003/0018332 A1 | 1/2003 | Schmaltz et al. | |
| 2006/0189981 A1 | 8/2006 | Dycus | |
| 2007/0106297 A1 | 5/2007 | Dumbauld | |
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0249776 A1 | 9/2010 | Kerr | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1920725 | 5/2008 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |
| WO | WO 2009/032623 | 3/2009 |

OTHER PUBLICATIONS

U.S. Appl. No. 09/591,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.

(56) References Cited

OTHER PUBLICATIONS

U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.

(56) References Cited

OTHER PUBLICATIONS

Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11180182.5 dated Nov. 4, 2011.

\* cited by examiner

DYNAMIC AND STATIC BIPOLAR ELECTRICAL SEALING AND CUTTING DEVICE

BACKGROUND

1. Technical Field

The present disclosure relates to a surgical forceps, and more particularly, to an electrosurgical forceps capable of sealing, cutting, and dissecting tissue.

2. Background of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can either cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. "Vessel sealing" is defined as the process of liquefying the collagen, elastin and ground substances in the tissue so that the tissue reforms into a fused mass with significantly-reduced demarcation between the opposing tissue structures.

Typically, once a vessel is sealed, the surgeon has to remove the sealing instrument from the operative site, substitute a new instrument, and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue seal.

Several attempts have been made to design an instrument which incorporates a knife or blade member which effectively severs the tissue after forming a tissue seal. For example, U.S. Pat. No. 5,674,220 to Fox et al. discloses a transparent instrument which includes a longitudinally reciprocating knife which severs the tissue once sealed. The instrument includes a plurality of openings which enable direct visualization of the tissue during the treatment and severing processes. This direct visualization allows a user to visually and manually regulate the closure force and gap distance between jaw members to reduce and/or limit certain undesirable visual effects known to occur when treating vessels, thermal spread, charring, etc. As can be appreciated, the overall success of creating an effective tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal along an ideal cutting plane.

U.S. Pat. No. 5,702,390 to Austin et al. discloses an instrument which includes a triangularly-shaped electrode which is rotatable from a first position to treat tissue to a second position to cut tissue. Again, the user must rely on direct visualization and expertise to control the various effects of treating and cutting tissue.

SUMMARY

In accordance with the present disclosure, an end effector assembly for use with an electrosurgical instrument, e.g., a forceps, is provided. The end effector assembly includes first and second jaw members disposed in opposed relation relative to one another. One or both of the jaw members are moveable relative to the other from an open position to a closed position in which the jaw members cooperate to grasp tissue therebetween. Each jaw member includes an electrically conductive tissue sealing surface adapted to connect to a source of electrosurgical energy such that the sealing surfaces are capable of conducting electrosurgical energy through tissue disposed between the jaw members. A static bipolar electrosurgical cutting portion is disposed on one or both of the jaw members and includes one or more electrically conductive cutting elements and one or more insulating elements having a first configuration. The static cutting portion electrically cuts tissue disposed between the jaw members upon activation of the cutting element and an opposing sealing surface and/or an opposing cutting element. A dynamic electrosurgical cutting portion is disposed on one or both of the jaw members and includes one or more electrically conductive cutting elements and one or more insulating elements having a second configuration. The dynamic cutting portion is configured for electrically transecting tissue during movement relative to tissue grasped between the jaw members.

In one embodiment, the end effector assembly is configured to operate in a first, sealing mode wherein the sealing surfaces are activated to seal tissue. The end effector assembly may also be configured to operate in a second, cutting mode, wherein the static cutting portion and/or the dynamic cutting portion are activated to cut tissue.

In another embodiment, the static cutting portion is disposed at a proximal end of an opposed surface of one or both of the jaw members and the dynamic cutting portion is disposed at a distal end of the opposed surface of one or both of the jaw members.

In yet another embodiment, the dynamic cutting portion is disposed on a longitudinal side of one or both of the jaw members.

In still another embodiment, the dynamic cutting portion is disposed on a distal tip of one or both of the jaw members.

In still yet another embodiment, each of the sealing surfaces includes a pair of spaced apart sealing surface sections. One or more of the insulating element(s) of the static cutting portion is disposed between the pair of spaced apart sealing surface sections. The electrically conductive cutting element of the static cutting portion may be partially disposed within the insulating element disposed between the pair of spaced apart sealing surface sections.

In yet another embodiment, the opposed surfaces of each of the jaw members are substantially symmetrical with respect to each other. Alternatively, the opposed surfaces of each of the jaw members may be substantially asymmetrical with respect to each other.

BRIEF DESCRIPTION OF THE DRAWINGS

Various embodiments of the subject instrument are described herein with reference to the drawings wherein.

DETAILED DESCRIPTION

Figure 1:
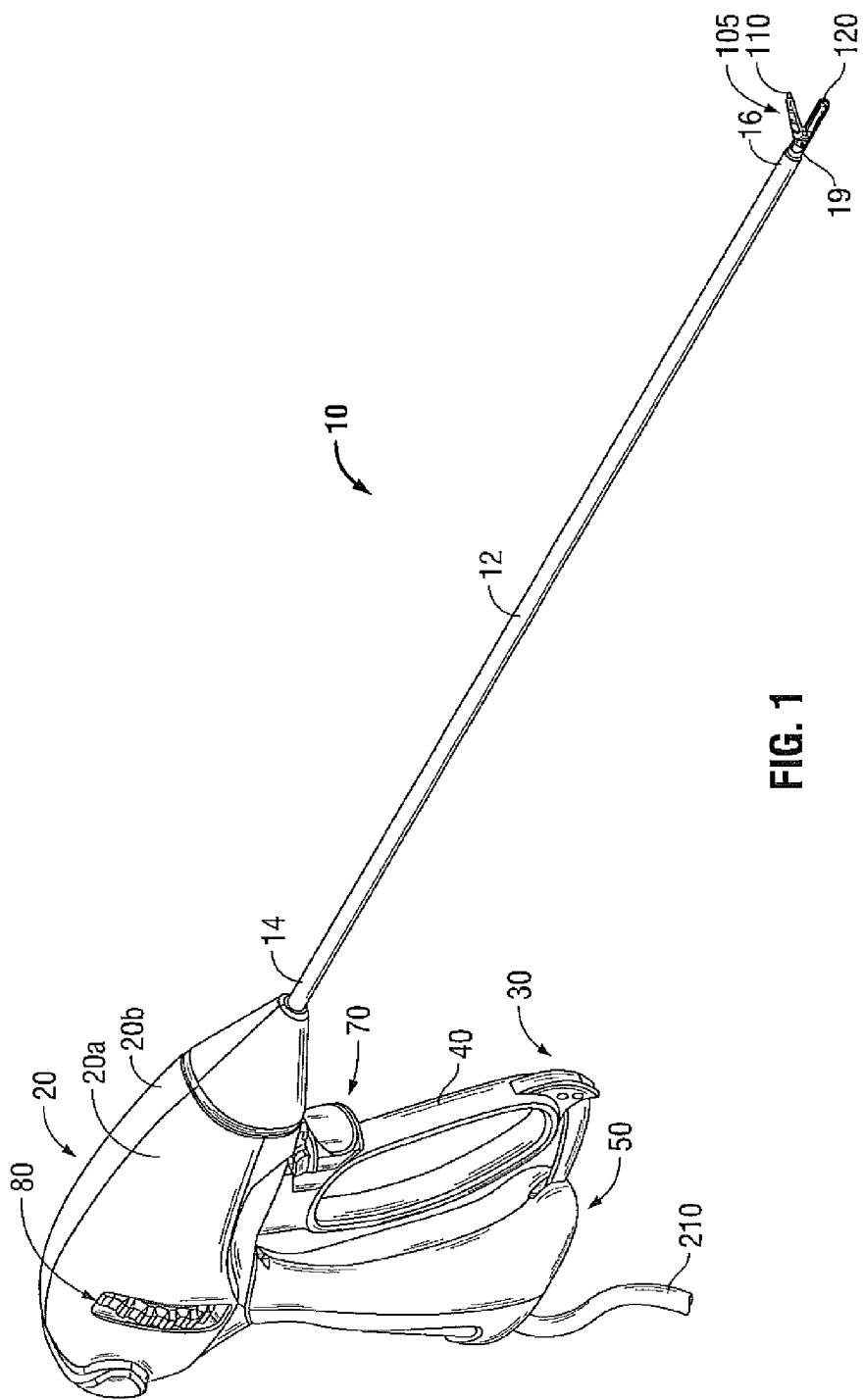
FIG. 1 is a right, perspective view of an endoscopic bipolar forceps including a housing, a shaft and an end effector assembly.
Figure 2:
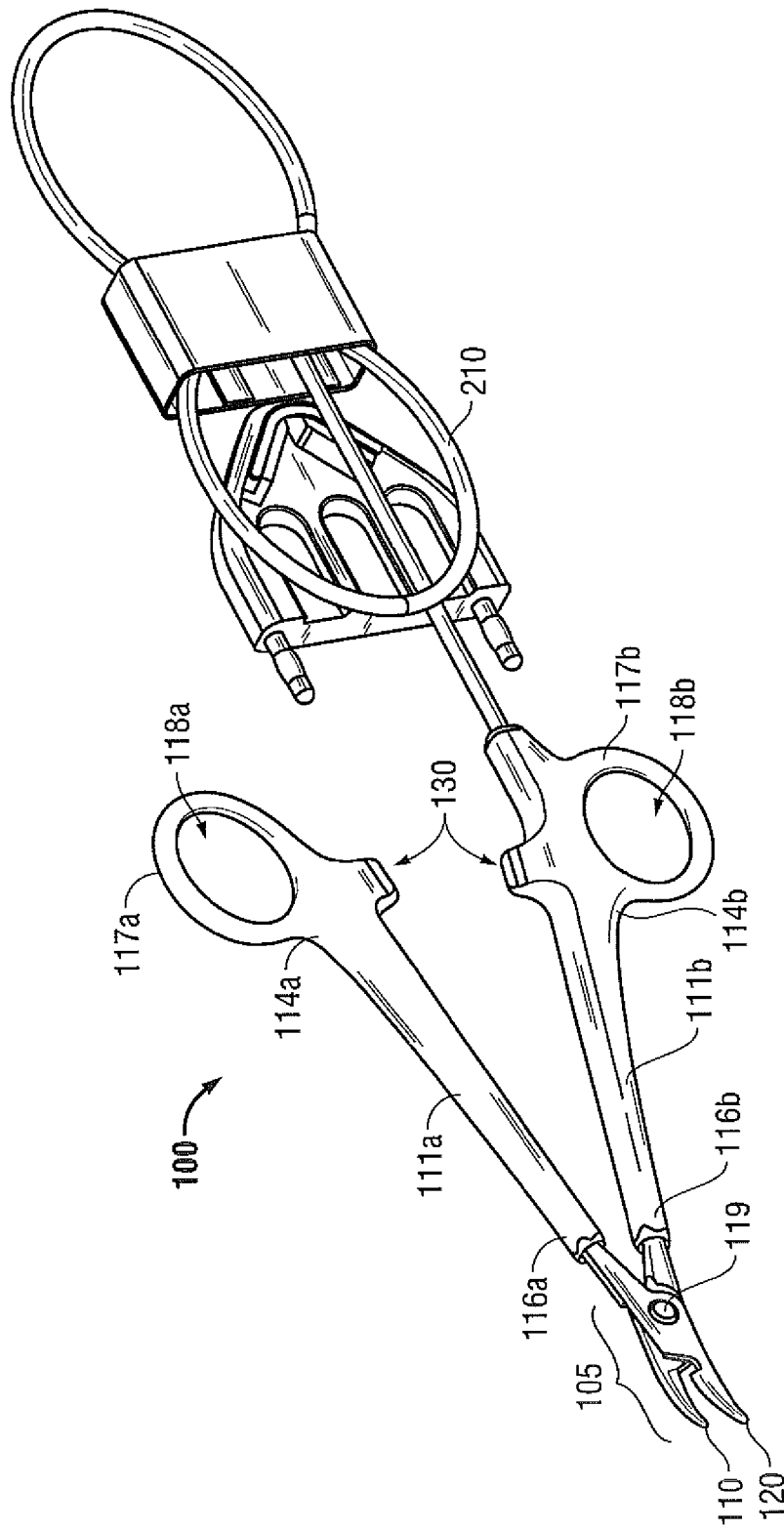
FIG. 2 is a left, perspective view of an open bipolar forceps showing a pair of first and second shafts having an end effector assembly disposed at a distal end thereof.

Referring now to FIGS. 1 and 2, FIG. 1 depicts a bipolar forceps 10 for use in connection with endoscopic surgical procedures and FIG. 2 depicts an open forceps 100 contemplated for use in connection with traditional open surgical procedures. For the purposes herein, either an endoscopic instrument or an open instrument may be utilized with the end effector assembly described herein. Obviously, different electrical and mechanical connections and considerations apply to each particular type of instrument, however, the novel aspects with respect to the end effector assembly and its operating characteristics remain generally consistent with respect to both the open or endoscopic designs.

FIG. 1 shows a bipolar forceps 10 for use with various endoscopic surgical procedures and generally includes a housing 20, a handle assembly 30, a rotating assembly 80, a switch assembly 70 and an end effector assembly 105 having opposing jaw members 110 and 120 that mutually cooperate to grasp, seal and divide tubular vessels and vascular tissue. More particularly, forceps 10 includes a shaft 12 that has a distal end 16 dimensioned to mechanically engage the end effector assembly 105 and a proximal end 14 that mechanically engages the housing 20. The shaft 12 may include one or more known mechanically engaging components that are designed to securely receive and engage the end effector assembly 105 such that the jaw members 110 and 120 are pivotable relative to one another to engage and grasp tissue therebetween.

The proximal end 14 of shaft 12 mechanically engages the rotating assembly 80 (the connection not shown in detail) to facilitate rotation of the end effector assembly 105. In the drawings and in the descriptions which follow, the term "proximal", as is traditional, will refer to the end of the forceps 10 which is closer to the user, while the term "distal" will refer to the end which is further from the user.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the end effector assembly 105 as explained in more detail below. Movable handle 40 and switch assembly 70 are of unitary construction and are operatively connected to the housing 20 and the fixed handle 50 during the assembly process. Housing 20 is constructed from two components halves 20a and 20b that are assembled about the proximal end of shaft 12 during assembly. Switch assembly 70 is configured to selectively provide electrical energy to the end effector assembly 105.

As mentioned above, end effector assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 2, an open forceps 100 includes a pair of elongated shaft portions 111a and 111b each having a proximal end 114a and 114b, respectively, and a distal end 116a and 116b, respectively. The forceps 100 includes jaw members 120 and 110 that attach to distal ends 116a and 116b of shafts 111a and 111b, respectively. The jaw members 110 and 120 are connected about pivot pin 119 which allows the jaw members 110 and 120 to pivot relative to one another from the first to second positions for treating tissue. The end effector assembly 105 is connected to opposing jaw members 110 and 120 and may include electrical connections through or around the pivot pin 119.

Each shaft 111a and 111b includes a handle 117a and 117b disposed at the proximal end 114a and 114b thereof which each define a finger hole 118a and 118b, respectively, therethrough for receiving a finger of the user. Finger holes 118a and 118b facilitate movement of the shafts 111a and 111b relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 is included for selectively locking the jaw members 110 and 120 relative to one another at various positions during pivoting.

As shown in FIGS. 1 and 2, forceps 10 or 100 also includes an electrical cable 210 that connects the forceps 10, 100 to a source of electrosurgical energy, e.g., an electrosurgical generator (not shown). Cable 210 extends through the shaft(s) 12, 111 to transmit electrosurgical energy through various electrical feed paths to the end effector assembly 105.

Figure 3A:
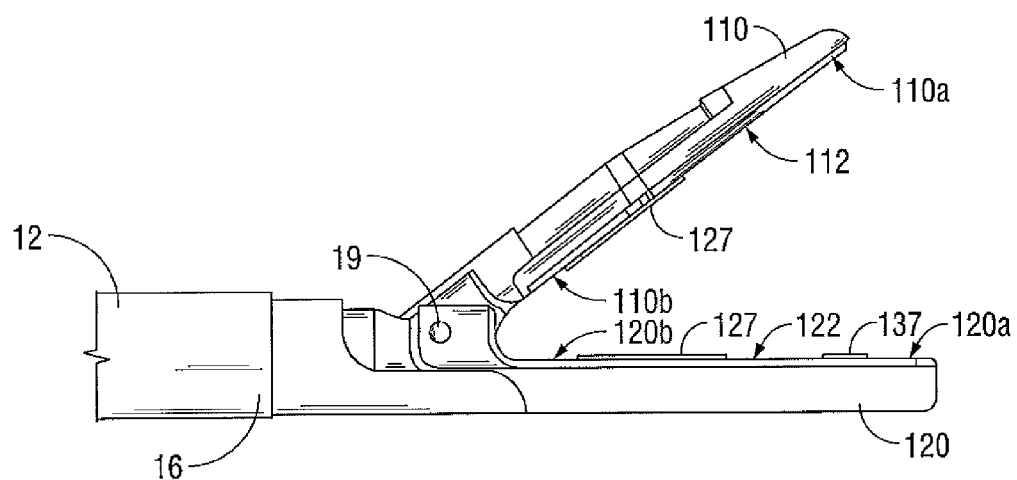
FIG. 3A is an enlarged, side view of the end effector assembly of FIG. 1 with a pair of jaw members in the open position.
Figure 3B:
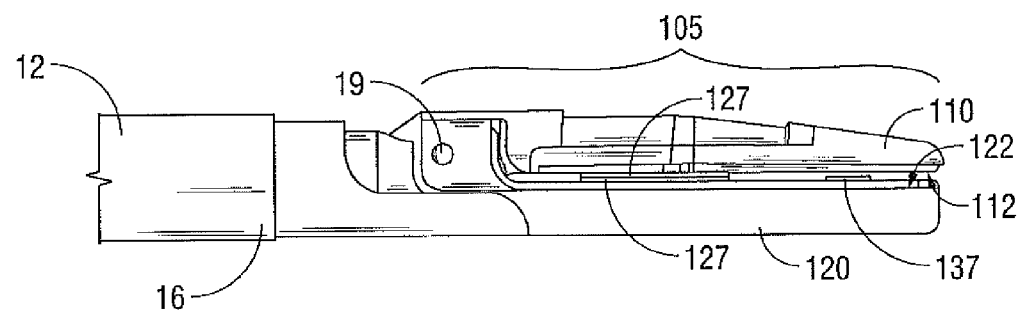
FIG. 3B is an enlarged, side view of the end effector assembly of FIG. 1 with the pair of jaw members in the closed position.

Referring now to the schematic illustrations of FIGS. 3A-3B, the jaw members 110 and 120 of both the endoscopic forceps of FIG. 1 and the open forceps of FIG. 2 include similar component features which cooperate to permit rotation about pivot 19, 119, respectively, to effect the grasping and sealing of tissue. Each jaw member 110 and 120 includes an electrically conductive tissue sealing plate 112 and 122, respectively. Tissue sealing plates 112, 122 of jaw members 110, 120, respectively, define opposed electrically conductive tissue sealing surfaces that cooperate to seal tissue. As shown in FIGS. 3A-3B, each jaw member 110 and 120 also includes a static bipolar cutting portion 127 disposed thereon, although it is also envisioned that only one of the jaw members 110, 120 need include a static cutting portion 127. Further, one (or both) jaw members, e.g., jaw member 120, includes a dynamic bipolar cutting portion 137. As shown in FIGS. 3A-3B, static cutting portions 127 are disposed toward proximal ends 110b, 120b of jaw members 110 and 120, respectively, while dynamic cutting portion 137 is disposed toward a distal end 120a of jaw member 120. However, static and dynamic bipolar cutting portions 127, 137, respectively, may be positioned at different locations on either or both of jaw members 110 and 120, as will be described in more detail below. The combination of sealing plates 112, 122, static cutting portion(s) 127 and dynamic cutting portion(s) 137 allows for sealing, static cutting, and dynamic dissection of tissue with a single surgical device 10, 100.

The various electrical connections of the end effector assembly 105 are configured to provide electrical continuity to the tissue sealing plates 112 and 122 and the cutting portions 127, 137 through the end effector assembly 105. For example, cable lead 210 (FIG. 1) may be configured to include four different leads (not shown) that carry different electrical potentials. The cable leads are fed through shaft 12 and connect to various electrical connectors (not shown) which ultimately connect to the electrically conductive sealing plates 112 and 122 and cutting portions 127, 137. The various electrical connections from cable lead 210 are dielectrically insulated from one another to allow selective and independent activation of either the tissue sealing plates 112 and 122 or the static and/or dynamic cutting portions 127, 137, respectively, as will be explained in more detail below. Alternatively, the end effector assembly 105 may include a single connector that includes an internal switch (not shown) to allow selective and independent activation of the tissue sealing plates 112, 122 and/or the cutting portions 127, 137.

Figure 4A:
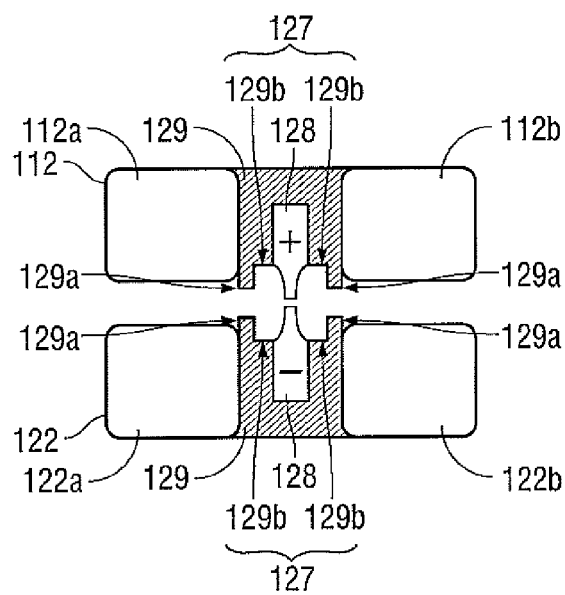
FIG. 4A is a schematic of one configuration of tissue sealing surfaces and static cutting portions that may be used with the end effector assembly of FIG. 1.
Figure 4B:
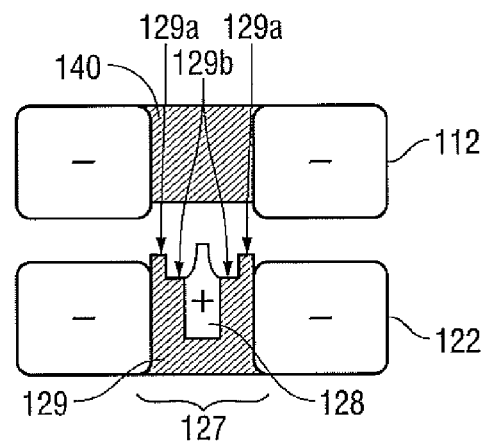
FIG. 4B is a schematic of another configuration of the tissue sealing surfaces and the static cutting portion that may be used with the end effector assembly of FIG. 1.

As best seen in FIGS. 4A-4B, several electrical configurations of the static cutting portion(s) 127 are shown which, in conjunction with the opposed sealing plates 112, 122, are designed to effectively seal and cut tissue disposed between opposing jaw members 110 and 120, respectively. The configuration of static cutting potion(s) 127 disposed between sealing plates 112, 122 shown in FIGS. 4A and 4B are example configurations designed to effect both tissue sealing and static tissue cutting, that is, tissue cutting wherein the jaw members 110, 120 remain stationary relative to tissue to be cut. More particularly, during a sealing mode, sealing plates 112 and 122 are activated to supply electrosurgical energy through tissue to effect a tissue seal. During a cutting mode, static cutting portion(s) 127 are activated to apply electrosurgical energy through tissue to effect tissue division. Other configurations of static cutting portions 127 capable of effecting both tissue sealing and cutting may be provided, such as those disclosed in commonly-owned U.S. Pat. No. 7,270,664 entitled "VESSEL SEALING INSTRUMENT WITH ELECTRICAL CUTTING MECHANISM," which is incorporated by reference herein. Further, it is envisioned that similar, or different configurations of the static cutting portions 127 may be provided on each of the jaw members 110, 120.

With reference to the embodiment of FIG. 4A, each of the static cutting portions 127 includes an insulator 129 and an electrically conductive cutting element 128 e.g., an electrically energizeable electrode. Insulators 129 are disposed between the electrically conductive sealing plates 112, 122 to divide each of the electrically conductive sealing plates 112, 122 into sections of electrically conductive sealing plates 112a, 112b and 122a, 122b on each jaw member 110 and 120, respectively. In other words, insulators 129 are disposed between sections 112a and 112b and sections 122a and 122b, of sealing plates 112 and 122, respectively. Each insulator 129 is generally centered between a respective tissue sealing plate 112a, 112b and 122a, 122b such that the two insulators 129 of the respective jaw members 110, 120 generally oppose one another. Further, each insulator 129 includes a pair of tabs 129a extending therefrom adjacent each of the sealing plate sections 112a, 112b, 122a, 122b and a recessed portion 129b defined between the tabs 129a and the electrodes 128.

The embodiment shown in FIG. 4B is substantially similar to the embodiment of FIG. 4A except that jaw member 110 includes an insulator 140 disposed between the sections 112a and 112b of sealing plate 112, rather than a static cutting portion 127 having both a cutting element 128 and an insulator 129.

The electrically conductive cutting elements 128 of static cutting portions 127 are disposed substantially within or disposed on the insulators 129. With respect to FIG. 4A, the cutting elements 128 are electrically conductive; however, one or both of the cutting elements 128 may be made from an insulative material with a conductive coating disposed thereon or one (or both) of the cutting elements may be non-conductive (not shown).

Figure 4C:
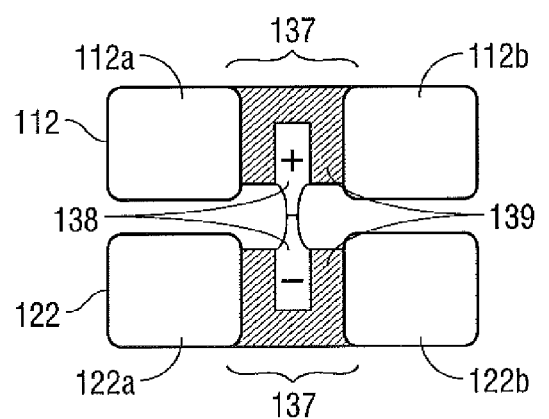
FIG. 4C is a schematic of one configuration of the tissue sealing surfaces and dynamic cutting portions that may be used with the end effector assembly of FIG. 1.
Figure 4D:
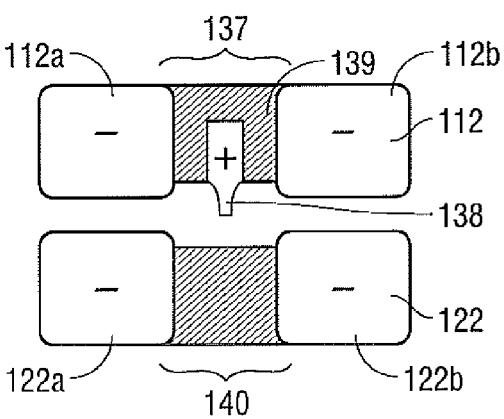
FIG. 4D is a schematic of another configuration of the tissue sealing surfaces and the dynamic cutting portion that may be used with the end effector assembly of FIG. 1.

With reference now to FIGS. 4C-4D, several electrical configurations of the dynamic cutting portion(s) 137 are shown. In FIGS. 4C-4D, the dynamic cutting portions 137 are shown disposed between electrically conductive sealing plate sections 112a, 112b and 122a, 122b of respective electrically conductive sealing plates 112, 122, similarly to the static cutting portions 127 shown in FIGS. 4A-4B and described above. In these embodiments, as shown in FIGS. 3A-3B, the static cutting portions 127 may be positioned between the sections 112a, 112b, 122a, 122b of sealing plates 112, 122 toward the proximal ends 110b and 120b of jaw members 110 and 120, respectively, while the dynamic cutting portions 137 are positioned between the sealing plates 112, 122 toward the distal ends 110a and 120a of the jaw members 110 and 120, respectively. This configuration may also be reversed, e.g., where the static cutting portions 127 are disposed toward the distal ends 110a and 120a and where the dynamic cutting portions 137 are disposed toward the proximal ends 110b and 120b of the jaw members 110 and 120, respectively. Further, as will be discussed in more detail below, the dynamic cutting portions 137 may be disposed in various other positions on either or both jaw members 110, 120.

As shown in FIG. 4C, the dynamic cutting portions 137 include an electrically conductive cutting element 138, e.g., an electrically energizeable electrode, positioned within and extending from an insulator 139 disposed between the electrically conductive sealing plates 112, 122, much like the configuration of the static cutting portions 127 discussed above (FIG. 4A-4B). The embodiment shown in FIG. 4D is similar to the embodiment of FIG. 4A except that jaw member 120 includes an insulator 140 disposed between the sections 122a and 122b of sealing plate 122 and does not include a cutting element 138 therein.

Insulators 139 of dynamic cutting portions 137 (FIGS. 4C-4D) are different from insulators 129 of static cutting portions 127 (FIGS. 4A-4B) in that the surfaces of insulators 139 are generally flat and do not include tabs or recesses. It has been found that this configuration of dynamic cutting portions 137, namely, the configuration of insulators 139, helps facilitate dissection, or dynamic tissue cutting, i.e., cutting of tissue while the jaw members 110 and/or 120 are moved relative to tissue. The configuration of static cutting portions 127 (FIGS. 4A-4B), on the other hand, has been found to help facilitate static electrosurgical cutting.

Put more generally, it has been found that some electrical configurations, e.g., the configuration of static cutting portions 127 (FIGS. 4A-4B), are more advantageous for static electrosurgical cutting, while other electrical configurations, e.g., the configuration of dynamic cutting portions 137 (FIGS. 4C-4D), are more advantageous for dynamic electrosurgical tissue dissection. Thus, the static cutting portions may define a variety of configurations, e.g., the configurations disclosed in commonly-owned U.S. Pat. No. 7,270,664 previously incorporated by reference herein or the configurations of FIGS. 4A-4B, which facilitate static electrosurgical cutting. The dynamic cutting portions may define a variety of configurations, including those disclosed in U.S. Pat. No. 7,270,664 or the configurations shown in FIGS. 4C-4D, which facilitate dynamic electrosurgical dissection. As mentioned above, the static and dynamic cutting portions may be configured differently, each configuration being adapted for a particular application, e.g., static or dynamic bipolar electrosurgical cutting.

With reference now to FIGS. 5A-9, dynamic cutting portions 137 are shown disposed at various positions on jaw member 120. Although dynamic cutting portions 137 are shown disposed on jaw member 120, it is envisioned that dynamic cutting portions 137 may be similarly disposed on jaw member 110 in cooperation with or in place of the dynamic cutting portions 137 of jaw member 120. Further, the positioning of dynamic cutting portions 137 shown in FIGS. 5A-9 are examples and other positions are contemplated.

Figure 5A:
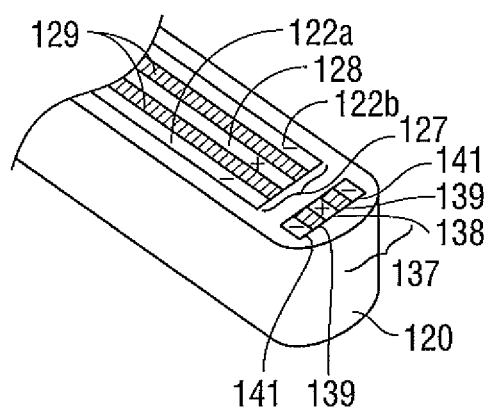
FIG. 5A is a front, perspective view of a bottom jaw member that may be used with the end effector assembly of FIG. 1 showing the tissue sealing surfaces and static and dynamic cutting portions according to another embodiment of the present disclosure.
Figure 5B:
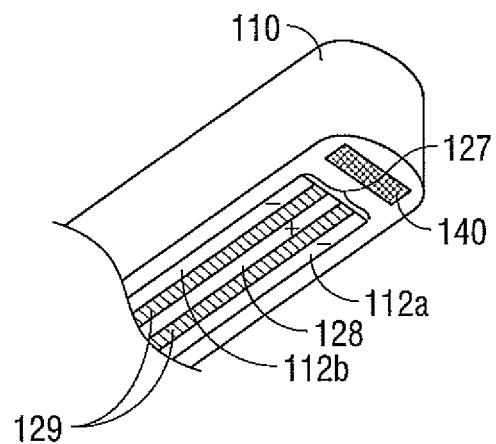
FIG. 5B is a rear, perspective view of a top jaw member that may be used with the end effector assembly of FIG. 1 showing the sealing surfaces and static cutting portion in accordance with yet another embodiment of the present disclosure.

FIG. 5A shows jaw member 120 including an electrically conductive sealing plate 122 including sealing plate sections 122a and 122b having static cutting portion 127 disposed therebetween. As mentioned above, static cutting portion 127 includes an electrically energizeable electrode, or cutting element 128, and a pair of insulators 129 configured for static electrosurgical cutting. Toward a distal end of jaw member 120, dynamic cutting portion 137 is shown including a dynamic cutting element 138 and a pair of insulators 139 configured for dynamic electrosurgical cutting. Sealing plate sections 122a and 122b may extend toward the distal end of jaw member 120 to surround the dynamic cutting portion 137, or, as shown in FIG. 5A, a pair of electrically conductive elements 141 may be positioned surrounding the insulators 139 to act as return electrode. As shown in FIG. 5B, jaw member 110 includes sealing plates 112a, 122b and static cutting portion 127 disposed therebetween. Jaw member 110 also includes an insulator 140 opposing dynamic cutting portion 137 of jaw member 120; however, jaw member 110 may include a dynamic cutting portion 137 in place of, or in addition to, dynamic cutting portion 137 disposed on jaw member 120.

Figure 6:
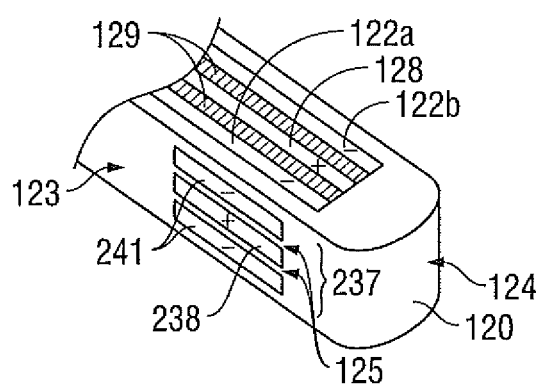
FIG. 6 is a front, perspective view of yet another embodiment showing the static and dynamic cutting portions of a bottom jaw member that may be used with the end effector assembly of FIG. 1.
Figure 7:
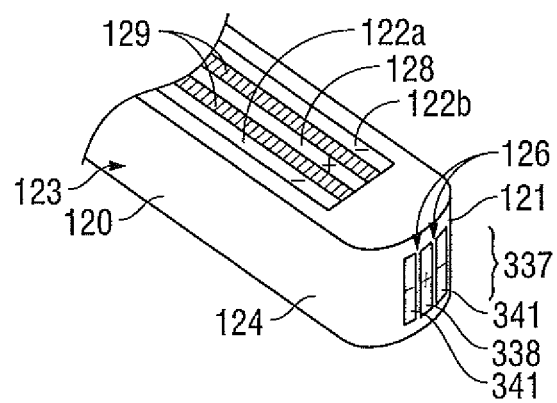
FIG. 7 is a front, perspective view of still yet another embodiment showing the static and dynamic cutting portions of a bottom jaw member that may be used with the end effector assembly of FIG. 1

FIGS. 6-9 illustrate various different positionings of the dynamic cutting portion. As shown in FIG. 6, a dynamic cutting portion 237 is disposed on a longitudinal side 123 of jaw member 120. Dynamic cutting portion 237 may be disposed on either longitudinal side 123 of jaw member 120 and for jaw member 110 and may be positioned toward a distal end 120a of the jaw member 120, or toward the proximal end 110b, 120b of either (or both) of the jaw members 110, 120, as desired. As shown in FIG. 7, a dynamic cutting portion 337 is disposed on a distal tip 121 of jaw member 120. Dynamic cutting portion 337 may be aligned vertically, as shown in FIG. 7, or may be aligned horizontally on jaw member 110 and/or jaw member 120.

Each dynamic cutting portion 237 and 337, shown in FIGS. 6 and 7, respectively, includes a cutting element 238, 338, which may be an electrically energizeable electrode 238, 338. Dynamic cutting portion 237, 337 also include insulators (not explicitly shown) which may be defined as the portion 125, 126 of insulated outer housing 124 of jaw member 120 surrounding the cutting element 238, 338. Further, a pair of electrically conductive elements, or return electrodes 241, 341 are provided surrounding the cutting element 238, 338, with the insulators, e.g., the portions 125, 126 of insulated outer housing 124, therebetween. It should be noted that dynamic cutting portions 137, 237, 337 are configured for bipolar electrosurgical cutting, e.g., each cutting portion 137, 237, 337 includes an electrically energizeable cutting element 138, 238, 338 and a pair of return electrodes, e.g., sealing plates 112, 122 or electrically conductive elements 141, 241, 341, thus obviating the need for a remote return pad, as is required for monopolar cutting.

Figure 8:
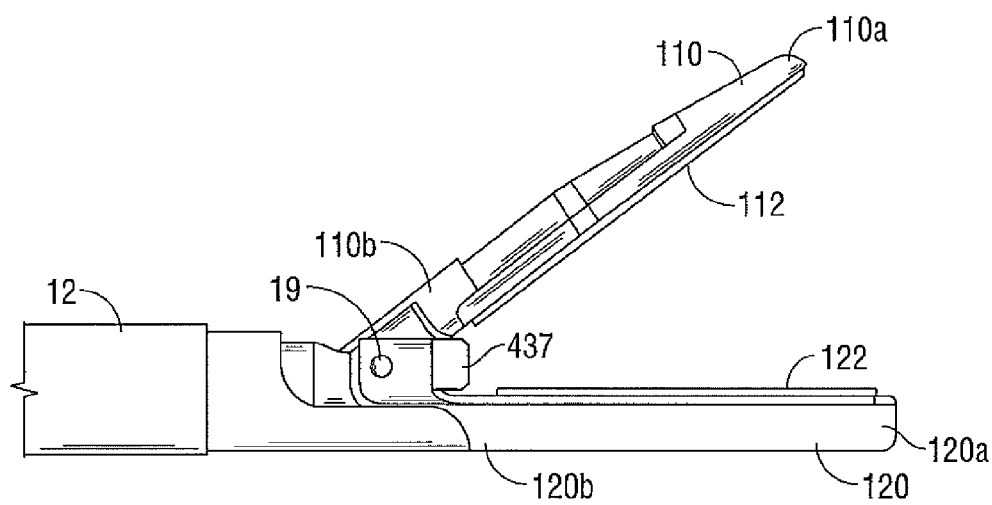
FIG. 8 is an enlarged, side view of yet another embodiment showing the dynamic cutting portion disposed adjacent a pivot of the jaw members of the end effector assembly of FIG. 1.

FIG. 8 shows another configuration wherein a dynamic cutting portion 437 is disposed adjacent pivot 19 of jaw members 110, 120. More particularly, dynamic cutting portion 437 is positioned between jaw members 110, 120 at proximal ends 110b, 120b, respectively, thereof such that, upon distal advancement of the forceps with jaw members 110, 120 in the open position, tissue disposed between jaw members 110, 120 may be electrically transected, or cut via dynamic cutting portion 437. Dynamic cutting portion 437 may be configured similarly to any of the dynamic cutting portions described above.

Figure 9:
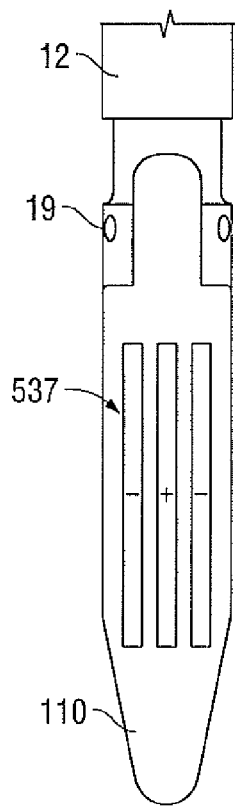
FIG. 9 is a top view of still another embodiment showing the dynamic cutting portion of a top jaw member that may be used with the end effector assembly of FIG. 1.

FIG. 9 shows yet another configuration wherein a dynamic cutting portion 537 is disposed on an outer, top surface of jaw member 110, although dynamic cutting portion 537 may alternatively be disposed on an outer, bottom surface of jaw member 120. Dynamic cutting portion 537 is configured for bipolar electrosurgical cutting, obviating the need for a remote return pad, as is required for monopolar cutting.

The operation of forceps 10 will now be described in detail. More specifically, the tissue sealing, static tissue cutting and dynamic tissue cutting modes, or phases of forceps 10 will be described with reference to FIGS. 5A-9. As shown in the drawings, the various polarities of the components are shown corresponding to the "cutting" phases, and thus do not represent the relative polarities of the components during the sealing phase.

To effect tissue sealing, forceps 10 is initially positioned such that jaw members 110 and 120 of end effector assembly 105 are disposed in the open position with tissue to be sealed therebetween. The jaw members 110, 120 are then moved to the closed position, clamping, or grasping tissue between electrically conductive sealing plates 112 and 122 of jaw members 110 and 120, respectively. The cutting elements 128 (and 138) are configured to extend from their respective insulators 129, respectively, beyond the sealing plates 112a, 112b and 122a and 122b such that the cutting elements 128 (and 138) act as stop members (i.e., create a gap distance "G" between opposing sealing surfaces of sealing plates 112 and 122) which promote accurate, consistent and effective tissue sealing.

During sealing, the opposing sealing plates 112a, 122a and 112b, 122b are activated, i.e., electrosurgical energy from a generator is supplied to sealing plates 112, 122 to seal the tissue disposed therebetween.

More specifically, during sealing, sealing plate 112 is energized to a first potential "+" and sealing plate 122 is energized to a second potential "−". The cutting element 128 is not energized. Since the insulator 129 does not conduct energy as well as the conductive sealing plates 112, 122, the first potential is not effectively or efficiently transferred to the cutting element 128 and the tissue is not necessarily heated or damaged during the sealing phase. During the sealing phase, energy is transferred from sealing plate sections 112a and 112b and through tissue to the return electrode, or return sealing plate sections 122a and 122b. As mentioned above, the static cutting element 128 of the static cutting portion 127 (and the dynamic cutting element 138 of dynamic cutting portion 137) mainly acts as a stop member for creating and maintaining a gap between the opposing sealing plates 112 and 122.

Once sealing is complete, the static cutting element(s) 128 may be independently activated, e.g., energized with electrosurgical energy, by the user or automatically activated by a generator (not shown) or other energy source to effect tissue cutting. During the static cutting mode, or phase, the electrical potential to sealing plates 112, 122 is turned off, static cutting element 128 of jaw member 110 is energized with a first electrical potential "+" and static cutting element 128 of jaw member 120 is energized with a second electrical potential "−" (see FIG. 4A). Alternatively, the static cutting element 128 of jaw members 120 may be energized with a first electrical potential "+" and opposing sealing plates 112 and 122 may be energized with a second electrical potential "−" (see FIG. 4B). In either embodiment, a concentrated electrical path is created between the potentials "+" and "−" through the tissue to cut the tissue between the previously formed tissue seal. Hence, tissue may be initially sealed and thereafter cut using the static electrosurgical cutting portion 127 without re-grasping the tissue.

However, it may be desirable, depending on the surgical procedure to be performed, to effect dynamic tissue dissection, or cutting, either before, after, or in place of tissue sealing and/or static cutting. To effect dynamic electrosurgical dissection, the dynamic cutting element 138, 238, 338 is activated to a first electrical potential "+" and the opposing sealing plates 112 and 122 (FIG. 4D) or electrically conductive elements 141, 241, 341 (FIGS. 5A-7) are activated to a second electrical potential "−". Alternatively, as shown in FIG. 4C, dynamic cutting element 138 of jaw member 110 may be activated to the first electrical potential "+" while dynamic cutting element 138 of jaw member 120 is activated to the second electrical potential "−". As with the static cutting portions 127, the activated dynamic cutting portions 137, 237, 337 create a concentrated electrical path between the potentials "+" and "−" to cut the tissue as the end effector assembly 105 is advanced through tissue. Jaw members 110 and 120 are opened slightly during translation of end effector assembly 105 in the embodiment of FIGS. 5A-5B to effect dynamic bipolar cutting of tissue. In the embodiments of FIGS. 6 and 9, end effector assembly 105 is translated laterally, in the direction of dynamic cutting portions 237, 537, respectively, to effect tissue dissection. The end effector assembly 105 is translated distally to effect electrosurgical tissue dissection via dynamic cutting portion 337, 437, in the embodiments of FIGS. 7 and 8, respectively.

Any combination of electrical potentials as described herein or in U.S. Pat. No. 7,270,664 may be utilized with the various jaw members 110, 120 and/or cutting portions 127, 137 to effectively seal tissue during an electrical sealing phase and cut tissue during static and/or dynamic electrical cutting phases. Further, sealing plates 112 and 122 of jaw members 110 and 120, static and dynamic cutting elements 128, 138, 238, 338 of static and dynamic cutting portions 127, 137, 237, 337, respectively, and/or electrically conductive element 141, 241, 341, may be energized with any combination of first and second electrical potential(s) (or other electrical potentials) to effectively seal and/or cut tissue.

As can be appreciated from the description above, the forceps 10, 100 is configured to operate in three modes or phases: (1) electrosurgical tissue sealing, (2) static bipolar electrosurgical cutting, and (3) dynamic bipolar electrosurgical cutting. The sealing plates 112, 122, the static cutting portions 127 and the dynamic cutting portions 137 are configured to seal, statically cut, and dynamically cut tissue, respectively. Thus, all three functions may be carried out with a single device, e.g. endoscopic forceps 10 or open forceps 100. It is envisioned that various manually operated and/or automatic switching mechanisms may be employed to alternate between the sealing and cutting modes.

Additionally, and particularly with reference to FIG. 1, forceps 10 may be configured as a handheld, battery-powered device. The battery (not shown) may be disposed within fixed handle 50 and may be configured to provide electrosurgical energy to the end effector assembly 105.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for use with an electrosurgical instrument, the end effector assembly comprising:
   first and second jaw members disposed in opposed relation relative to one another, at least one of the jaw members moveable relative to the other from a first, open position to a second, closed position wherein jaw members cooperate to grasp tissue therebetween;
   each jaw member including an electrically conductive tissue sealing surface adapted to connect to a source of electrosurgical energy such that the sealing surfaces are capable of conducting electrosurgical energy through tissue disposed between the jaw members;
   a static electrosurgical cutting portion disposed on at least one of the jaw members, the static cutting portion including at least one first electrically conductive cutting element and at least one first insulating element positioned adjacent the at least one first electrically conductive cutting element, the at least one first insulating element configured and dimensioned to define a first configuration for electrically cutting tissue statically retained between the jaw members upon activation of the at least one first electrically conductive cutting element; and
   a dynamic electrosurgical cutting portion disposed on at least one of the jaw members, the dynamic cutting portion including at least one second electrically conductive cutting element and at least one second insulating element positioned adjacent the at least one second electrically conductive cutting element, the at least one second insulating element configured and dimensioned to define a second configuration, different from the first configuration, for electrically transecting tissue upon movement of the dynamic electrosurgical cutting portion relative to tissue with the at least one second electrically conductive cutting element activated.

2. The end effector assembly according to claim 1, wherein the end effector assembly is configured to operate in a first, sealing mode wherein the sealing surfaces are activated to seal tissue.

3. The end effector assembly according to claim 1, wherein the end effector assembly is configured to operate in a second, cutting mode wherein at least one of the static cutting portion and the dynamic cutting portion is activated to cut tissue.

4. The end effector assembly according to claim 1, wherein the static cutting portion is disposed at a proximal end of an opposed surface of at least one of the jaw members and wherein the dynamic cutting portion is disposed at a distal end of the opposed surface of at least one of the jaw members.

5. The end effector assembly according to claim 1, wherein the dynamic cutting portion is disposed on a longitudinal side of at least one of the jaw members.

6. The end effector assembly according to claim 1, wherein the dynamic cutting portion is disposed on a distal tip of at least one of the jaw members.

7. The end effector assembly according to claim 1, wherein each of the sealing surfaces includes a pair of spaced apart sealing surface sections and wherein the at least one first insulating element is disposed between the pair of spaced apart sealing surface sections.

8. The end effector assembly according to claim 7, wherein the at least one first electrically conductive cutting element is at least partially disposed within the at least one first insulating element disposed between the pair of spaced apart sealing surface sections.

9. The end effector assembly according to claim 1, wherein opposed surfaces of each of the jaw members are substantially symmetrical with respect to each other.

10. The end effector assembly according to claim 1, wherein opposed surfaces of each of the jaw members are substantially asymmetrical with respect to each other.

* * * * *